(12) United States Patent
Naimark et al.

(10) Patent No.: US 7,455,657 B2
(45) Date of Patent: Nov. 25, 2008

(54) METHOD AND APPARATUS TO MODIFY A FLUID USING A SELECTIVELY PERMEABLE MEMBRANE

(75) Inventors: Wendy Naimark, Cambridge, MA (US);
Susan O'Brien, Boston, MA (US);
Brandon Shuman, Kirkland, WA (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 1543 days.

(21) Appl. No.: 09/883,178

(22) Filed: Jun. 19, 2001

(65) Prior Publication Data

US 2002/0193732 A1   Dec. 19, 2002

(51) Int. Cl.
*A61M 37/00* (2006.01)
*A61M 25/00* (2006.01)

(52) U.S. Cl. ........................ 604/82; 604/523

(58) Field of Classification Search .............. 604/5.01, 604/6.09, 27, 29, 35, 43, 44, 48, 93.01, 181, 604/187, 190, 264, 272, 523, 890.1, 82–92
See application file for complete search history.

(56) References Cited

U.S. PATENT DOCUMENTS

| | | | |
|---|---|---|---|
| 2,901,112 A * | 8/1959 | Naftulin et al. ............... 210/94 |
| 3,592,245 A * | 7/1971 | Schneller et al. ............. 141/25 |
| 3,851,650 A * | 12/1974 | Darling ...................... 604/129 |
| 3,965,896 A * | 6/1976 | Swank ....................... 604/6.07 |
| 4,016,864 A | 4/1977 | Sielaff et al. |
| 4,265,249 A | 5/1981 | Schindler et al. |
| 4,552,555 A * | 11/1985 | Theeuwes ................... 604/85 |
| 4,844,871 A * | 7/1989 | Polaschegg ................. 422/81 |
| 4,891,225 A | 1/1990 | Langer et al. |
| 4,938,763 A | 7/1990 | Dunn et al. |
| 4,953,561 A * | 9/1990 | Guirguis .................... 604/318 |
| 5,372,582 A | 12/1994 | Skrabal et al. |
| 5,397,354 A | 3/1995 | Wilk et al. |
| 5,443,481 A | 8/1995 | Lee |
| 5,591,404 A | 1/1997 | Mathewson |
| 5,632,897 A | 5/1997 | Mathieu |
| 5,747,058 A | 5/1998 | Tipton et al. |
| 5,792,469 A | 8/1998 | Tipton et al. |
| 5,833,652 A * | 11/1998 | Preissman et al. ............. 604/82 |
| 5,888,533 A | 3/1999 | Dunn |

(Continued)

FOREIGN PATENT DOCUMENTS

DE   32 15 003   11/1983

(Continued)

*Primary Examiner*—Kevin C. Sirmons
*Assistant Examiner*—Elizabeth R MacNeill
(74) *Attorney, Agent, or Firm*—Kenyon & Kenyon LLP (57) ABSTRACT

Method and apparatus to modify a fluid by passing a compound through a selectively permeable membrane is provided. In one embodiment a fluid moving through a vessel is modified prior to its ejection from the vessel. This may be accomplished by urging the fluid into a mixing chamber wherein the mixing chamber is in fluid communication with an exit orifice and a passageway. This passageway may be in communication with a second chamber through a selectively permeable membrane. The fluid may then be altered by passing a compound between the mixing chamber and the second chamber through the passageway and the selectively permeable membrane. A device for modifying a fluid moving through a vessel may contain a first lumen, a second lumen, an exit orifice, and a mixing chamber in communication with the first lumen and the exit orifice.

13 Claims, 4 Drawing Sheets

U.S. PATENT DOCUMENTS

| | | |
|---|---|---|
| 5,945,115 A | 8/1999 | Dunn et al. |
| 5,990,194 A | 11/1999 | Dunn et al. |
| 6,045,565 A | 4/2000 | Ellis et al. |
| 6,372,482 B1 * | 4/2002 | Mitrani .................... 435/284.1 |
| 6,758,828 B2 * | 7/2004 | Hammer et al. ............... 604/43 |

FOREIGN PATENT DOCUMENTS

| | | |
|---|---|---|
| DE | 32 15 003 A1 | 11/1983 |
| EP | 0 780 133 | 12/1995 |
| GB | 2 268 066 | 5/1994 |
| WO | WO 89 01794 | 3/1989 |
| WO | WO 00 16826 | 3/2000 |

* cited by examiner

METHOD AND APPARATUS TO MODIFY A FLUID USING A SELECTIVELY PERMEABLE MEMBRANE

TECHNICAL FIELD

The present invention regards modifying the composition of a fluid as the fluid travels through a lumen. More specifically the present invention relates to the use of a selectively permeable membrane to facilitate the modification of a fluid moving through a lumen by passing a compound through the selectively permeable membrane prior to the ejection of the fluid from the lumen.

BACKGROUND

Modifying the composition of a compressible or non-compressible fluid prior to its ejection from a lumen is a desirable step with numerous far-reaching applications. For example, by modifying a non-compressible fluid prior to its ejection from a lumen, the fluid may be stored in one state and then changed or modified into another state, one that is more useful or beneficial for the task at hand.

With regard to certain medical procedures, it may be advantageous, for example, for a therapeutic being delivered to a target site in the body to rapidly solidify upon its disposition into the target site. In one specific example, when therapeutic is injected into an actively contracting tissue, such as the myocardium of the heart, the therapeutic may be susceptible to being ejected or squeezed back out through its point of entry. This unwanted discharge of the therapeutic can result in an unascertainable dosage of therapeutic being actually administered to the myocardium as well as the unwanted interface between the expelled therapeutic and neighboring tissue and organs. Thus, in order to combat this unwanted discharge solid plugs may be formed encapsulating the therapeutic to retard its ejection from the target site.

While it may be beneficial to employ a therapeutic having a high solids content, therapeutic with a high solid to fluid ratio may resist passage though its delivery lumen. In some cases a solvent may be used to provide an operative balance of solids to fluids. In these cases, however, the solvent employed may be toxic in relation to the delivery site or incompatible with the therapeutic.

When the solvent is toxic it may be toxic in certain applications but not in others. For example, ethanol, which maybe used as a solvent, is generally considered "bio-compatible," however, this is clearly not the case when the target site is within the myocardium. This selective toxicity is problematic at least to the extent that a medical device carrying a therapeutic could not be universally employed but would, rather, only be usable for target sites that were not injured by the solvent.

To counter this potential toxicity with the target and the unwanted incompatibility with the therapeutic a less than optimum amount of solvent may be used. Alternatively, a proper amount of solvent may be used at the risk of unwanted side effects stemming from its use. In both cases the effectiveness of the therapeutic may be compromised.

SUMMARY OF THE INVENTION

Method and apparatus to modify a fluid by passing a compound through a selectively permeable membrane are provided. In one embodiment a fluid moving through a vessel is modified prior to its ejection from the vessel. This may be accomplished by urging the fluid into a mixing chamber wherein the mixing chamber is in fluid communication with an exit orifice and a passageway. This passageway may be in communication with a second chamber through a selectively permeable membrane. The fluid may then be altered by passing a compound between the mixing chamber and the second chamber through the passageway and the selectively permeable membrane.

A device for modifying a fluid moving through a vessel may contain a first lumen, a second lumen, an exit orifice, and a mixing chamber in communication with the first lumen and the exit orifice. In this device the mixing chamber may have a passageway fluidly connecting it to the second lumen and containing a selectively permeable membrane that may be positioned to selectively pass compounds through the passageway.

DETAILED DESCRIPTION

Figure 1:
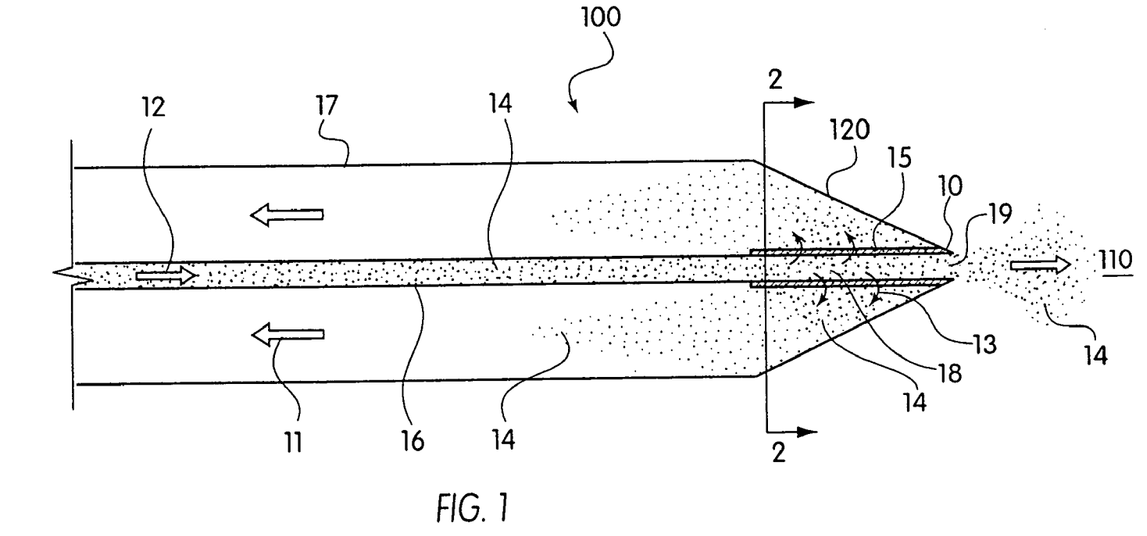
FIG. 1 is an enlarged side sectional view of the distal end of a dual lumen catheter in accordance with an embodiment of the present invention.

FIG. 1 is an enlarged side sectional view of the distal end of a dual lumen catheter 100 having a piercing tip 10 in accordance with an embodiment of the present invention. In FIG. 1, outer lumen 17, inner lumen 16, solvent 14, mixing chamber 18, selectively permeable membrane 15, exit orifice 19, and piercing tip 10 are clearly evident. Also evident in FIG. 1 are vacuum force arrows 11, pushing force arrows 12, and solvent direction of travel arrows 13. In the catheter 100 of FIG. 1 the inner lumen 16 is located within the outer lumen 17 and shares a concentric longitudinal axis with the outer lumen 17. The outer lumen 17 has tapered ends 120, in this embodiment, which end or terminate in the piercing tip 10.

When the catheter shown in FIG. 1 is used to inject a therapeutic into a target site located deep within the body, it may be necessary to form the outer lumen and the piecing tip of the catheter with a rigid material such as a medical grade stainless steel or a highly rigid polymer so that it may withstand the internal forces generated in storing and delivering the therapeutic and the external forces associated with delivering the therapeutic to a target site.

The inner lumen 16 in FIG. 1 is shown located in the center of the outer lumen 17. The inner lumen 16 is also shown in connection with and in fluid communication with a mixing chamber 18 which has a selectively permeable membrane 15 encircling it. This mixing chamber 18, as can be seen, is in contact with both the inner lumen 16 and the exit orifice 19. It is here, in the mixing chamber 18, that therapeutic traveling down the inner lumen 16 can be modified through the insertion or deletion of compounds into the therapeutic prior to its ejection from the catheter via the exit orifice 19.

The pushing force arrow 12 demonstrates the direction of a force that may be generated at the proximal end of the catheter and used to urge the therapeutic through the inner lumen 16. Similarly, a vacuum forced arrow 11 is also illustrated, to show the direction of a vacuum force that may be generated at the proximal end of the catheter and used to draw compounds through the selectively permeable membrane 15 of the mixing chamber 18. In this embodiment the passing of the solvent through the selectively permeable membrane 15 is accelerated by the vacuum force 11 resident in the outer lumen 17.

In this figure, the solvent 14 is shown dispersed within inner lumen 16, outer lumen 17, mixing chamber 18, and target site of the body 110. As can be seen, the density of solvent 14 per unit volume varies depending on its location within and outside of the device.

In use the catheter 100 would be inserted into the target site 110 to deliver a therapeutic resident within the inner lumen 16. After the catheter 100 has been inserted into the target site 110 the therapeutic containing the solvent may be pushed down the inner lumen 16 through various means including a syringe, a mechanical pump and a squeezable bladder. These means may be used not only to push the therapeutic through the lumen but also to store it prior to the catheter being used and to control the volume and rate of injection of the therapeutic.

When the therapeutic being employed has a high solid to liquid ratio a solvent 13 may be mixed into the therapeutic. In this example, as the therapeutic is pushed into the mixing chamber 18 the solvent 14 may migrate out of the therapeutic, through the selectively permeable membrane, and into the outer lumen 17, thus lowering the solid to liquid ratio of the therapeutic. After leaving the mixing chamber, now containing plugs and having a lower solid to liquid ratio, the therapeutic may be better suited to remain within an actively contracting target site 110.

While the removal of solvent is described above, other modifications, either in place of or in addition to the removal of the solvent, may be made to the therapeutic as well. For example, as described below, a hardening agent may be added to the therapeutic as it passes through the mixing chamber or the solvent may be removed and the hardening agent may be added.

In addition, by adding or removing compounds, various chemical reactions may also be performed within the mixing chamber 18 prior to the fluid being ejected through the exit orifice 19. These reactions could include the introduction of reducing agents, cross-linking agents, and various other agents, some of which are discussed in more detail below.

The vacuum force shown in FIG. 1 may be generated by various devices located at the proximal end of the catheter including a vacuum pump, a syringe, and an aspirating tube. This vacuum force, as indicated above, assists in removing the solvent from the therapeutic traveling through the mixing chamber 18.

In addition to using the vacuum force to supplement the removal of solvent from the therapeutic within the mixing chamber 18 of the device other methodologies may also be used. For example, centripetal forces may be generated in the mixing chamber by rotating the chamber or the entire device to facilitate the transfer of the solvent out of the therapeutic and through. the selectively permeable membrane. Moreover, chemical forces, ionic attractions, particulate sizes, and hydrophobic affinities may also be applied to selectively draw or push compounds through the selectively permeable membranes.

The selectively permeable membrane may be made from any appropriate material. The membrane may be chosen predicated upon the specific application of the catheter, upon the specific therapeutic passing through the mixing chamber or upon any combination of fluids and applications that may be encountered. A polycarbonate membrane is an example of a selectively permeable membrane 15 that may be used in certain applications. Other plausible examples are glass microfibers, PTFE (Teflon™), polyethersulfone, nylon, polypropylene, cellulose including that having enzyme-linked surfaces, antibodies, chelating agents, absorbent coatings, and functional modifications of these materials.

Figure 2:
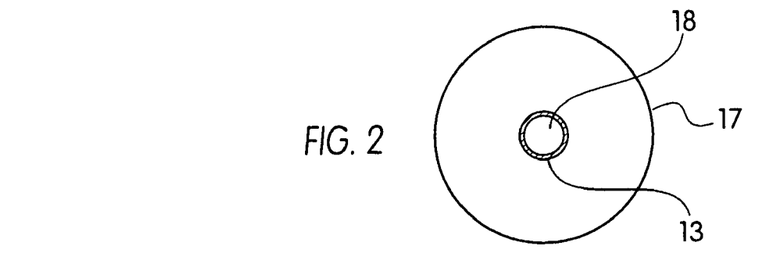
FIG. 2 is a cross-sectional view taken along line 2-2 of FIG. 1.

FIG. 2 is a cross-section taken along line 2-2 of FIG. 1. As can be seen in FIG. 2, the selectively permeable membrane 13, which defines the mixing chamber 18, may be circular and may be concentrically located within the outer lumen 17. While the mixing chamber 18 and the outer lumen 17 do share the same longitudinal axis in this embodiment, other embodiments are also plausible. For example, the mixing chamber 18 and the outer lumen 17 do not need to share the same longitudinal axis but may, instead, be parallel lumens sharing an outer wall.

Figure 3:
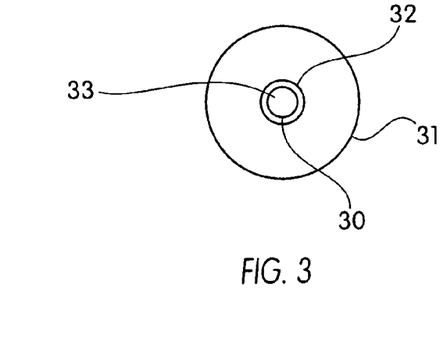
FIG. 3 is a cross-sectional view of the distal end of a catheter in accordance with an alternative embodiment of the present invention.

FIG. 3 is a cross-sectional view taken through the distal end of a catheter in accordance with an alternative embodiment of the present invention. The location of the section of the catheter of FIG. 3 is similar to the location of the section illustrated in FIG. 2. As can be seen in FIG. 3, a mixing chamber 33, a wire support 32, an outer lumen 31, and a selectively permeable membrane 30 are all provided. In this embodiment, the wire support 32, which may be an expandable stent, may be used to support the selectively permeable membrane such that the membrane may be better suited to withstand the forces placed on it by the fluid as the fluid is pushed through the mixing chamber 33.

Figure 4:
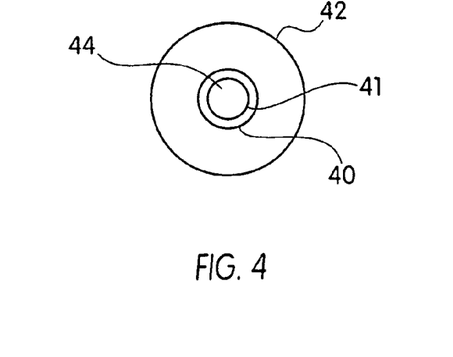
FIG. 4 is a cross-sectional view of the distal end of a catheter in accordance with another alternative embodiment of the present invention.

FIG. 4 also shows a cross-sectional view taken through the distal end of a catheter, similar to the location of the cross-sectional view of FIG. 2. In FIG. 4, the mixing chamber 44, the outer lumen 42, the wire support 41, and the selectively permeable membrane 40 are all clearly evident. Opposite to the embodiment illustrated in FIG. 3, the wire support 41 in FIG. 4, which may also be an expandable stent or any other hollow structure that can provide adequate structural support, is located within the selectively permeable membrane 40 and provides support from the inside surface of the membrane 40. In this embodiment, the wire would contact the therapeutic or other fluid passing through the mixing chamber 44 and would, accordingly, need to be compatible with that fluid.

Comparatively, depending upon the specific application, the design of the wire support 41 may be modified or changed to facilitate various fluid flow patterns resident within the mixing chamber and passing through the membrane 40. For example, the wire support 41 may have a large profile projecting into the mixing chamber to help facilitate the reduction of speed and the increase in turbulence of the fluid moving through the mixing chamber—thereby increasing the rate of transposition of the compound through the selectively permeable membrane 40. Alternatively, the wire support 41 may have a very low profile to allow fluid moving through the mixing chamber to retain its speed, have a low degree of turbulence as it passes through the mixing chamber 44, and, thus, a low transfer rate through the selectively permeable membrane 40.

In both figures, FIG. 3 and FIG. 4, the mixing chamber may be manufactured separately from the device by dipping or otherwise coating the wire support, concomitantly with the manufacture of the device or, alternatively, through various other methods that will be evident to one of skill in the art.

Figure 5:
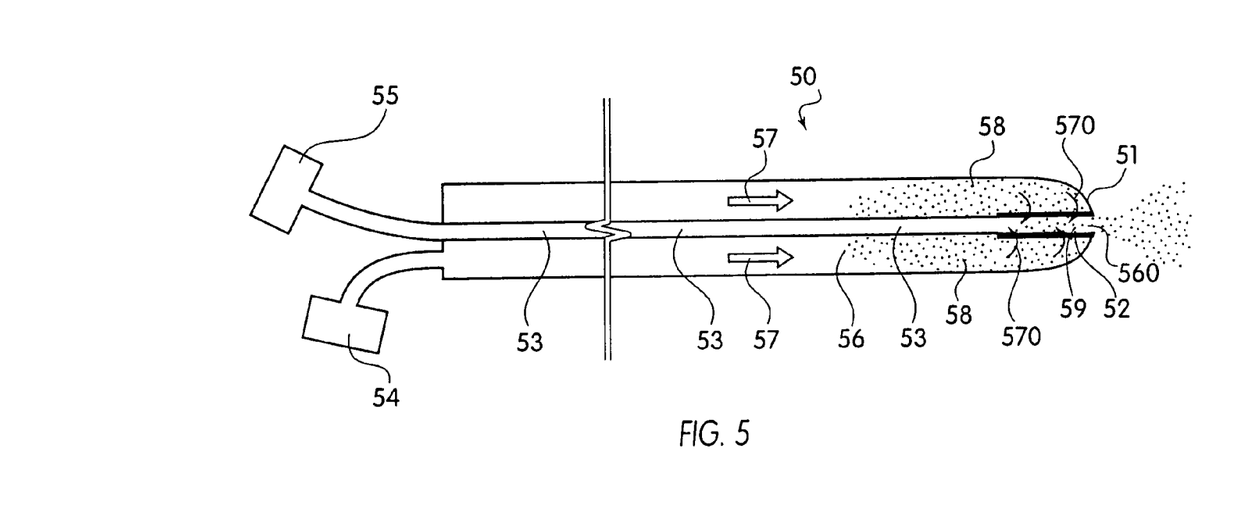
FIG. 5 is a side sectional view of a dual lumen catheter in accordance with another alternative embodiment of the present invention.

FIG. 5 is a side view of a dual lumen catheter in accordance with another alternative embodiment of the present invention. In FIG. 5, a first pressure pump 55, a second pressure pump 54, an inner lumen 53, an outer lumen 56, pressure arrows 57, a hardening agent 58, a rounded distal end 51, a mixing chamber 59, and selectively permeable membranes 52 are illustrated. In this embodiment, the first pressure pump 55 and the second pressure pump 54 are used to force a therapeutic and a hardening agent towards the distal end of the dual lumen catheter 50. The first pressure pump 55, which may be any commercially available pressure pump, including a hand-operated squeezable bladder, a syringe removably fixed to the distal end of the catheter, and a micro-pump. All of these may be used to specifically measure the amount of therapeutic being injected into the inner lumen 53. In the embodiment of FIG. 5 the first pressure pump may be in fluid communication with the inner lumen 53 while the second pressure pump 54 may be in fluid communication with the outer lumen 56.

Like the first pressure pump, the second pressure pump 54 may also be any type of device that may be used to apply pressure to a fluid located within the outer lumen 56. In this embodiment both pressure pumps are located at the proximal end of the dual lumen catheter 50 although they may be located at other positions of the catheter as will be recognized by one of skill in the art.

In FIG. 5, pressure arrows 57 indicate the direction of the force and resultant pressure being applied by second pressure pump 54 to the hardening agent 58 located within the outer lumen 56. The hardening agent 58, which is solely illustrated near the distal end of the dual lumen catheter 50, will be understood by one of skill in the art to be resident within the entire outer lumen 56. Upon receiving pressure from the second pressure pump 54, hardening agent 58, resident within the outer lumen 56, may be squeezed through the selectively permeable membrane 52, as shown by hardening agent flow arrows 570, enter the mixing chamber 59 and directly contact the therapeutic 560 resident within the mixing chamber 59. Upon coming in contact with the hardening agent 58, the fluid therapeutic 560 may precipitate out and harden to form controlled release plugs which can forestall the therapeutic from being squeezed or released from an actively contracting target area.

Rather than having a piercing tip, as in the above embodiments, the embodiment of FIG. 5 contains a rounded distal end 51 which may be inserted into the target site with little or no damage to the site. This rounded distal end 51 may be used to facilitate a greater transfer of compound between the outer lumen 56 and the inner lumen 53 through the selectively permeable membrane 52 as a greater amount of space is available behind the membrane 52 at its most distal location. Also, rather than using an applied pressure as depicted in FIG. 3, cationic, anionic, and other chemical forces may, instead, be used to urge the hardening agent 58 or any other compound through the selectively permeable membrane 52.

In the embodiment depicted in FIG. 5, the hardening agent 58 may be, for example, thrombin, and the therapeutic 560, traveling through the inner lumen 53, may be, for example, fibrinogen. In this example, as the fibrinogen passed through the mixing chamber 59, and as the thrombin passed into the mixing chamber, they would react and cause the solution to polymerize at the point of exit from the dual lumen catheter 50.

Figure 6:
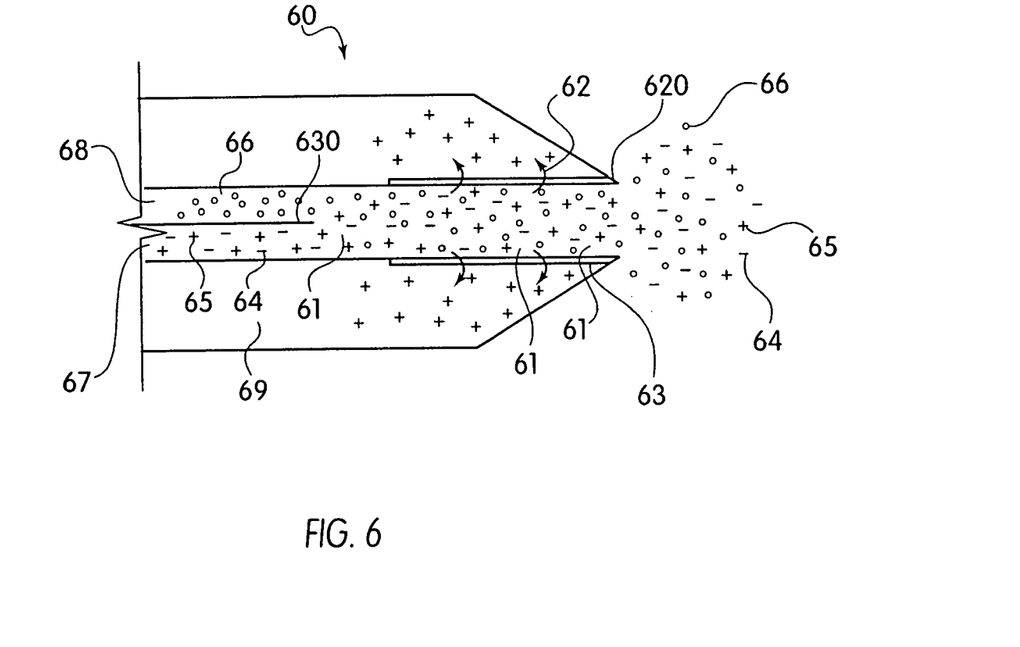
FIG. 6 is an enlarged side sectional view of the distal end of a multi-lumen needle in accordance with an alternative embodiment of the present invention.

FIG. 6 is a side sectional view of the distal end of a needle 60. In FIG. 6, a first inner lumen 67, a second inner lumen 68, a solvent flowing through the membrane 62, a hardening agent 66, a solvent 65, a therapeutic 64, a membrane 63, a piercing tip 620, and an outer lumen 69 are illustrated.

The embodiment of FIG. 6 illustrates how the present invention may be used within a needle. In this embodiment, three lumens are employed. The first two, the first inner lumen 67 and the second inner lumen 68, are located about a longitudinal axis of the needle 60 and within the outer lumen 69, while the third one, the outer lumen 69, encircles them both.

In contrast to the earlier embodiments, the mixing chamber 61 is not completely defined by the membrane 63. Rather, as can be seen, the end of the wall 630, which separates the first inner lumen 67 and the second inner lumen 68, marks the beginning of the mixing chamber 61 while the piercing tip 620 marks the end of the mixing chamber. By providing a first and a second area within the mixing chamber, two different reactions or desired mixing combinations can be facilitated. First, the solvent 65 and the therapeutic 64 traveling down the first inner lumen 67 may come in contact with the hardening agent 66 in the first portion of the mixing chamber prior to them reaching the membrane 63. There, these three components can first begin to be mixed. Then, after initially being mixed, the three components or compounds can be pushed down the first and the second inner lumens to the second portion of the mixing chamber 61 which contains the membrane 63. There, in the second portion of the mixing chamber 61, the solvent can flow and be drawn through the membrane 63 into the outer lumen 69.

In so doing, the fluid that leaves the distal end of the needle 60 contains a higher proportion of therapeutic 64 and hardening agent 66 and a lower proportion of solvent 65 than originally combined in the first part of the mixing chamber 61. By mixing these compounds together in this fashion, the in situ formation of controlled release plugs can be completed. These release plugs may be beneficial to retaining therapeutic within an actively contracting and expanding target site of the body.

In one specific embodiment a monomer may be placed within the first inner lumen 67 and a catalyst may be placed within the second inner lumen 68. These two may first be combined in the initial area of the mixing chamber 61. The catalyst may then be removed as the fluid passes through the mixing chamber 61 prior to its exit from the piecing tip 620.

While mechanical forces and size exclusion may be used to exert pressure against the membrane 63 and draw the solvent through the membrane as illustrated by arrow 62, other forces, as suggested above, may also be used. These include chemical forces that attract the solvent or any other desired compound through the membrane including ionic and hydrophobic interactions.

The outer lumen 69 in this embodiment may be made from any suitably rigid material including surgical stainless steel, nitinol, and rigid plastics. Similarly, the internal lumens may also be made from any suitably rigid material capable of carrying fluids that preferably will also be compatible with the therapeutics or other fluids traveling through them. The therapeutics traveling through the inner lumen in this embodiment as well as in the other embodiments may include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

Organs and tissues that may be treated by the methods of the present invention include any mammalian tissue or organ, whether injected in vivo or ex vivo. Non-limiting examples include heart, lung, brain, liver, skeletal muscle, smooth muscle, kidney, bladder, intestines, stomach, pancreas, ovary, prostate, eye, tumors, cartilage and bone.

The therapeutic agents can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

Figure 7:
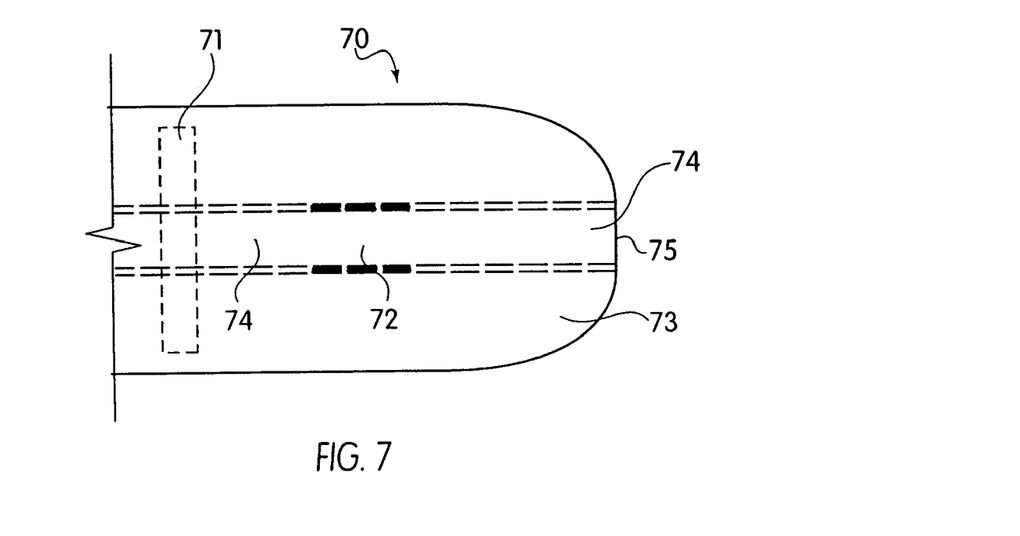
FIG. 7 is an enlarged side view of the distal end of a dual lumen catheter in accordance with another alternative embodiment of the present invention.

FIG. 7 is the side view of the distal end of a catheter 70 in accord with another alternative embodiment of the present invention. In FIG. 7, a mixing chamber 72, passageways 74, a distal tip 73, and a resin block 71 are evident. In this embodiment, the mixing chamber 72 is not directly touching the distal tip 73, but, is rather, in communication with it through the passageway 74, which is itself in contact with the exit orifice 75.

Depending upon the specific application and the specific fluid traveling through the inner lumen, it may be advantageous to modify the length of the passageway such that a certain amount of time passes from when the compound is first inserted or removed from the fluid to the time that the fluid is actually ejected from the catheter 70. This time may be used to facilitate further thickening or further modification of the fluid prior to its ejection from the catheter after its initial modification in the mixing chamber 72. Moreover, although not shown in this illustration, the temperature of the fluid may be changed as the fluid passes through the passageway 74 closest to the exit orifice 75 to further modify the fluid prior to its ejection from the exit orifice 75.

The resin block 71 shown in this illustration may be used to create chemical or ionic forces to draw compounds from the fluid passing through the mixing chamber and also to store those compounds within the catheter 70 after their removal from the fluid. The resin block may also function to prevent the compounds from being reintroduced into the fluid at a later time should the catheter 70 be used in a subsequent or second procedure. The resin block in this embodiment may be permanently fixed in the catheter 70 or it may be replaceable to reuse the catheter 70. Likewise, various other components of this and the other embodiments may also be replaceable as will be evident to one of skill in the art.

Other applications or embodiments of the current invention are also plausible. For example, the internal mixing chambers may also be employed in chromatograph distillation tubes to facilitate the sampling of compounds exiting these tubes. In addition a plunger or other mechanism may be employed to purge the mixing chamber between applications.

Figure 8:
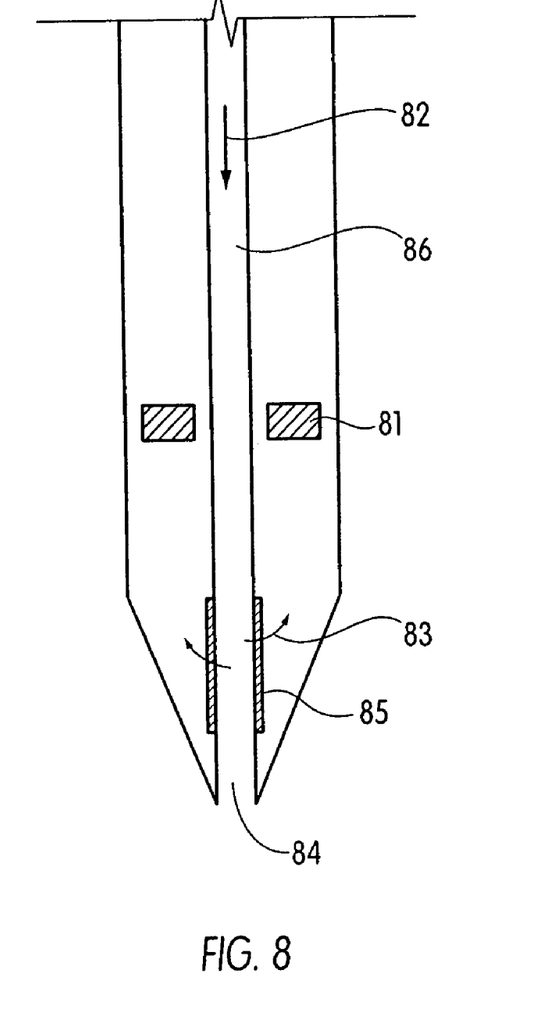
FIG. 8 is a side sectional view of the distal end of a chromatography distillation tube in accordance with another alternative embodiment of the present invention.

In FIG. 8 a side sectional view of the distal end of a chromatography distillation tube 80, in accord with another alternative embodiment of the present invention, is shown. Sample direction arrow 82, resin block 81, impurity removal arrow 83, selectively permeable membranes 85, and mixing chamber 84 are all clearly evident in FIG. 8. In the embodiment of FIG. 8 a sample resident within a carrier fluid moving down the internal lumen 86 towards the mixing chamber 84 would come in contact with the selectively permeable membrane 85. This selectively permeable membrane 85 may be chosen to be permeable to only certain compounds or impurities that may be resident within the sample moving through the internal lumen 86 or to perhaps the carrier fluid itself. Upon entering the mixing chamber 84, these impurities or compounds may pass through the selectively permeable membrane and may be drawn to or attracted to the resin 81 which may then retain or store these impurities or compounds. The purified sample may then exit the chromatography distillation tube 80 to be sampled or tested by the larger chromatography unit (which is not shown).

Method and apparatus to modify a fluid using a selectively permeable membrane is provided. Various embodiments are described above including its use in the delivery of therapeutics in medical procedures as well as its use in the sampling of fluids in chromatographic applications. It should be appreciated that other embodiments, modifications, and variations of the present invention are also plausible and may be made without departing from the spirit and scope of the present invention.

What is claimed is:

1. A device for modifying a fluid moving through a vessel prior to the ejection of the fluid from the vessel into the body of a patient, the device comprising:
   a first lumen;
   a second lumen;
   an exit orifice located at a distal end of the first lumen;
   a mixing chamber positioned within the first lumen proximal to the exit orifice, the mixing chamber in communication with the exit orifice, and
   a passageway located proximal to the exit orifice, the passageway being positioned between the mixing chamber and the second lumen and fluidly connecting the mixing chamber to the second lumen, the second lumen being connected to the mixing chamber at a location proximal to the exit orifice, the passageway containing a selectively permeable membrane positioned to selectively pass compounds through the passageway between the mixing chamber and the second lumen;
   wherein the selectively permeable membrane is adapted to extract a compound from fluid in the mixing chamber and into the second lumen.

2. The device of claim 1 further comprising:
   a third lumen, the third lumen in fluid communication with the mixing chamber, and the mixing chamber in direct contact with the exit orifice.

3. The device of claim 1 further comprising:
   a vacuum source in fluid communication with the second lumen; and,
   a resin positioned within the second lumen, the resin adapted to trap and retain compounds passing through the selectively permeable membrane and resident within the second lumen.

4. The device of claim 1 wherein the selectively permeable membrane is adapted to extract a solvent from fluid in contact with the selectively permeable membrane and wherein the mixing chamber is in direct contact with the exit orifice.

5. The device of claim 4 wherein the fluid is a therapeutic.

6. The device of claim 1 wherein the material comprising the first lumen includes a metal.

7. The device of claim 1 wherein the selectively permeable membrane comprises a polycarbonate.

8. The device of claim 1 wherein the selectively permeable membrane comprises glass microfibers.

9. The device of claim 1 wherein the mixing chamber is sized to fit within an internal lumen of the body of the patient.

10. A catheter for delivering a fluid inside the body of a patient, the catheter comprising:
    a first lumen for transporting the fluid from a proximal end of the catheter to a distal end of the catheter, the first lumen comprising an exit orifice at the distal end of the catheter through which the fluid is discharged to the patient;
    wherein the catheter further comprises:
    a fluid modification chamber located within the first lumen proximal to the exit orifice;
    a second lumen connected by a passageway to the fluid modification chamber, the passageway being connected to the fluid modification chamber at a location proximal to the exit orifice of the first lumen; and
    a selectively permeable membrane located in the passageway between the fluid modification chamber and the second lumen, wherein the selectively permeable membrane is positioned to selectively pass compounds through the passageway between the fluid modification chamber and the second lumen, thereby modifying the fluid prior to the fluid being discharged through the exit orifice;
    wherein the selectively permeable membrane is adapted to extract a compound from fluid in the fluid modification chamber and into the second lumen.

11. The catheter of claim 10 wherein the selectively permeable membrane is adapted to extract a solvent from the fluid while the fluid is in the fluid modification chamber.

12. The catheter of claim 10 wherein the selectively permeable membrane is adapted to add a compound to the fluid while the fluid is in the fluid modification chamber.

13. A device for modifying a fluid moving through a vessel prior to the ejection of the fluid from the vessel comprising:
    a first lumen;
    a second lumen;
    an exit orifice located at a distal end of the first lumen;

a mixing chamber in communication with the first lumen and the exit orifice; and a passageway located proximal to the exit orifice, the passageway being positioned between the mixing chamber and the second lumen and fluidly connecting the mixing chamber to the second lumen, the second lumen being connected to the mixing chamber at a location proximal to the exit orifice, the passageway containing a selectively permeable membrane positioned to selectively pass compounds through the passageway;

wherein the first lumen and the second lumen are concentric about one another and share a longitudinal axis; and wherein the selectively permeable membrane is adapted to extract a compound from fluid in the mixing chamber and into the second lumen.

* * * * *

UNITED STATES PATENT AND TRADEMARK OFFICE
CERTIFICATE OF CORRECTION

| | |
|---|---|
| PATENT NO. | : 7,455,657 B2 |
| APPLICATION NO. | : 09/883178 |
| DATED | : November 25, 2008 |
| INVENTOR(S) | : Naimark et al. |

It is certified that error appears in the above-identified patent and that said Letters Patent is hereby corrected as shown below:

In the Drawing Figure:
Figure 2, reference numeral "13" should be changed to reference number --15--.

Column 1, line 40, "though" should be changed to --through--;
Column 1, line 46, "maybe" should be changed to --may be--;
Column 1, line 55, "therapeutic a" should be changed to --therapeutic, a--;
Column 1, line 63, "Method" should be changed to --A method--;
Column 2, line 11, "device the" should be changed to --device, the--;
Column 2, line 59, "piecing tip" should be changed to --piercing tip--;
Column 3, line 11, "forced arrow" should be changed to --force arrow--;
Column 3, line 23, "In use the" should be changed to --In use, the--;
Column 3, line 25, "110 the" should be changed to --110, the--;
Column 3, line 34, "solvent 13" should be changed to --solvent 14--;
Column 3, line 36, "chamber 18 the" should be changed to --chamber 18, the--;
Column 4, lines 19-20, "selectively permeable membrane 13" should be changed to --selectively permeable membrane 15--;
Column 6, line 3, "the membrane 62" should be changed to --the membrane shown by arrow 62--;
Column 6, line 45, "piecing tip 620" should be changed to --piercing tip 620--;
Column 7, lines 5-6, "viral, liposomes" should be changed to --viral liposomes--;
Column 7, line 31, "lisidomine" should be changed to --linsidomine--;
Column 7, line 37, "Warafin" should be changed to --warfarin--;
Column 7, line 39, "promotors" should be changed to --promoters--;
Column 7, line 41, "promotors" should be changed to --promoters--;
Column 7, line 49, "vascoactive" should be changed to --vasoactive--;
Column 8, line 23, "("BMP's")" should be changed to --("BMPs")--;
Column 8, line 26, "BMP's" should be changed to --BMPs--;
Column 8, line 33, "DNA's" should be changed to --DNAs--;
Column 9, line 25, "tube 80" should be changed to --tube--; and
Column 9, line 42, "tube 80" should be changed to --tube--.

Signed and Sealed this
Twenty-seventh Day of September, 2011

David J. Kappos
*Director of the United States Patent and Trademark Office*